(12) United States Patent
Hynes

(10) Patent No.: US 10,639,124 B2
(45) Date of Patent: May 5, 2020

(54) TRANSPORTATION CONTAINER FOR A MEDICAL DEVICE

(71) Applicant: KeyMed (Medical & Industrial Equipment) Ltd, Essex (GB)

(72) Inventor: John Hynes, Essex (GB)

(73) Assignee: KEYMED (MEDICAL & INDUSTRIAL EQUIPMENT) LTD (GB)

( * ) Notice: Subject to any disclaimer, the term of this patent is extended or adjusted under 35 U.S.C. 154(b) by 165 days.

(21) Appl. No.: 15/568,815

(22) PCT Filed: Apr. 28, 2016

(86) PCT No.: PCT/GB2016/051201
§ 371 (c)(1),
(2) Date: Oct. 24, 2017

(87) PCT Pub. No.: WO2016/174435
PCT Pub. Date: Nov. 3, 2016

(65) Prior Publication Data
US 2018/0110580 A1    Apr. 26, 2018

(30) Foreign Application Priority Data
Apr. 30, 2015    (GB) .................................. 1507424.8

(51) Int. Cl.
*A61B 50/36*    (2016.01)
*A61B 1/00*    (2006.01)
(Continued)

(52) U.S. Cl.
CPC .......... *A61B 50/36* (2016.02); *A61B 1/00144* (2013.01); *A61M 25/002* (2013.01);
(Continued)

(58) Field of Classification Search
CPC ................ A61B 50/36; A61B 1/00144; A61B 2090/701; A61B 2050/314;
(Continued)

(56) References Cited

U.S. PATENT DOCUMENTS 515,928 A  *  3/1894  Thompson ........... A45C 7/0031
                                                      190/104
618,442 A  *  1/1899  Shearer ................. B65D 37/00
                                                      220/9.2
(Continued)

FOREIGN PATENT DOCUMENTS

EP    2491810 A1    8/2012
FR    3001718       2/2013
(Continued)

OTHER PUBLICATIONS

Patents Act 1977: Search Report under Section 17, Application GB1507424.8, date of search Sep. 29, 2015.
(Continued)

*Primary Examiner* — Ernesto A Grano
(74) *Attorney, Agent, or Firm* — Luedeka Neely Group, PC

(57) ABSTRACT

A container for carrying a medical instrument such as an endoscope after use and before cleaning, comprises a perimeter wall having a height h and defining an enclosure with a diameter d. The perimeter wall is substantially rigid in the height dimension. A flexible base and a flexible cover are attached to the wall. The wall is compressible to a reduced diameter configuration for storage and expandable to an increased diameter configuration for use. The wall may comprise a series of adjacent panels foldable concertina-style to reduce the diameter.

10 Claims, 4 Drawing Sheets

(51) Int. Cl.
*A61M 25/00* (2006.01)
*A61B 50/00* (2016.01)
*A61B 50/30* (2016.01)
*A61B 90/70* (2016.01)

(52) U.S. Cl.
CPC .............. *A61B 2050/0071* (2016.02); *A61B 2050/3011* (2016.02); *A61B 2050/314* (2016.02); *A61B 2090/701* (2016.02)

(58) Field of Classification Search
CPC ... A61B 2050/0071; A61B 2050/3011; A61M 25/002
USPC .......................................................... 206/363
See application file for complete search history.

(56) References Cited

U.S. PATENT DOCUMENTS

| | | | | |
|---|---|---|---|---|
| 756,311 | A * | 4/1904 | Adams | B65D 5/36 229/117.05 |
| 1,086,007 | A | 2/1914 | Wollitzer | |
| 1,555,115 | A * | 9/1925 | Hand | A47G 29/06 383/33 |
| 1,940,596 | A * | 12/1933 | Koppelman | B65D 77/0426 229/90 |
| 2,586,078 | A * | 2/1952 | O'Malley | B65D 85/04 206/397 |
| 2,807,405 | A * | 9/1957 | Lambert | B65D 3/22 229/117.01 |
| 3,670,946 | A * | 6/1972 | Croley | B65D 5/12 229/4.5 |
| 3,902,541 | A * | 9/1975 | Wardwell | A45C 7/0063 217/44 |
| 4,764,029 | A | 8/1988 | Abblett | |
| 4,792,086 | A * | 12/1988 | Chen | A45F 3/20 229/117 |
| 5,048,977 | A * | 9/1991 | Robbins | B65D 1/42 383/104 |
| 5,213,253 | A * | 5/1993 | Fantoni | A45C 7/0036 229/117 |
| 5,287,903 | A * | 2/1994 | Ambasz | A45C 7/0022 150/129 |
| D370,138 | S * | 5/1996 | Rosebrock | D6/349 |
| D374,844 | S * | 10/1996 | Weder | D11/164 |
| 5,695,447 | A | 12/1997 | Yabe et al. | |
| 5,752,649 | A * | 5/1998 | Weder | A01G 9/026 220/495.06 |
| 5,938,646 | A | 8/1999 | Carter | |
| 5,988,492 | A * | 11/1999 | Capy | B65D 75/28 229/122.34 |
| D434,698 | S * | 12/2000 | Weder | D11/164 |
| 6,170,712 | B1 * | 1/2001 | Kasboske | B65D 1/32 222/107 |
| 6,223,932 | B1 * | 5/2001 | Usui | B65D 1/0292 215/382 |
| 6,234,384 | B1 * | 5/2001 | Capy | B65D 65/12 156/519 |
| 6,474,472 | B1 * | 11/2002 | Shaw | A61M 5/3205 206/366 |
| 7,077,571 | B1 * | 7/2006 | Wilson | B65F 1/02 220/908 |
| 7,946,764 | B2 * | 5/2011 | Sulpizio | B65D 33/007 383/104 |
| D651,818 | S * | 1/2012 | Omori | D6/349 |
| D653,079 | S * | 1/2012 | King | D7/400 |
| 8,328,043 | B2 * | 12/2012 | Kessell | B65D 1/40 220/666 |
| D734,666 | S * | 7/2015 | Blonder | D9/430 |
| D810,452 | S * | 2/2018 | Gu | D6/352 |
| 2004/0066987 | A1 * | 4/2004 | O'Neill | B65D 31/04 383/75 |
| 2005/0023282 | A1 | 2/2005 | Murrer, III | |
| 2005/0249439 | A1 * | 11/2005 | Penson | D06F 95/004 383/38 |
| 2007/0036472 | A1 * | 2/2007 | Persenda | B65D 33/28 383/33 |
| 2007/0280568 | A1 * | 12/2007 | Levy | B65D 31/06 383/120 |
| 2008/0056625 | A1 * | 3/2008 | Stanton | B65F 1/0006 383/104 |
| 2010/0059531 | A1 * | 3/2010 | Smith | B65D 5/36 220/666 |
| 2011/0052838 | A1 * | 3/2011 | Levkovitch | A01K 1/0125 428/12 |
| 2011/0215205 | A1 * | 9/2011 | Sutphen | B65F 1/06 248/97 |
| 2016/0235225 | A1 * | 8/2016 | Lehovetzki | A47G 9/062 |
| 2018/0242764 | A1 * | 8/2018 | Wynne | A47G 23/0216 |

FOREIGN PATENT DOCUMENTS

| | | |
|---|---|---|
| GB | 2507780 A | 5/2014 |
| WO | 2011061600 A2 | 5/2011 |
| WO | 2011094411 A1 | 8/2011 |

OTHER PUBLICATIONS

Authorized Officer Martin Schindler, European Patent Office, International Search Report, PCT/GB2016/051201, date of search Jul. 18, 2016.

The International Bureau of WIPO, Geneva, Switzerland PCT International Preliminary Report on Patentability, dated Oct. 31, 2017 PCT/GB2016/051201.

* cited by examiner

TRANSPORTATION CONTAINER FOR A MEDICAL DEVICE

CROSS-REFERENCE TO RELATED APPLICATION

This application claims priority under all applicable statutes, and is a U.S. National phase (37 U.S.C. Section 371) of International Application PCT/GB2016/051201, filed Apr. 26, 2016, and entitled TRANSPORTATION CONTAINER FOR A MEDICAL DEVICE, which claims priority to GB 1507424.8, filed Apr. 30, 2015, incorporated herein by reference in their entireties.

The present invention relates to a transportation container for a medical device such as an endoscope. The container can be stored in a compressed state and expanded when needed to provide an enclosure large enough to fit the medical device.

After carrying out a medical procedure with a device such as an endoscope, the device is contaminated with body fluids and must be thoroughly cleaned and sterilised before it is used again. The cleaning process is normally carried out at a different location and so the endoscope must be transported safely, in a manner which protects it from damage and prevents it contaminating anything else. Typically, the endoscope may be placed in a flexible bag which is sealed for transport and later disposed of when the endoscope is cleaned. Alternatively, endoscopes may be placed in a rigid plastic tray for transport and cleaning. A plastic sheet may then be sealed over the cleaned tray and endoscope so they are ready for a subsequent re-use.

The present invention provides a container for carrying a medical instrument, comprising a perimeter wall having a height and defining an enclosure with a diameter, wherein the perimeter wall is substantially rigid in its height dimension, a flexible base attached to the outer wall on which a medical device can be received, and an openable and a closeable flexible cover attached to the outer wall, wherein the wall is compressible into a reduced diameter configuration for storage and expandable to an increased diameter configuration for receiving a medical device.

In this way, a container is provided which can be stored in a compressed form for space efficiency and expanded easily when desired. It provides improved protection for the medical instrument during transport but can be disposed of after use.

The perimeter wall may comprise a plurality of adjacent panels with fold lines therebetween. There may be multiple panels which are folded concertina-style. Alternatively, the wall may comprise two panels joined at their ends by fold lines.

The flexible base, or the flexible cover, or both may comprise a thin flexible sheet material. The cover is preferably in the form of a substantially tubular sheet with first and second circular edges, wherein the first circular edge is secured to the perimeter wall and the second circular edge is free and provided with a closure means, which may comprise a drawstring.

The perimeter wall may define two or more apertures for receiving a user's fingers to facilitate to carrying the container. Conveniently, the perimeter wall may be formed of corrugated cardboard.

A fluid absorbent sheet may be located within the container to increase the ability to carry any fluid present on a medical instrument.

Preferably, the flexible base does not protrude below a lowermost edge of the perimeter wall when the container is in its expanded configuration.

The invention will now be described in detail, by way of example only, with reference to the accompanying drawings, in which.

Figure 1:
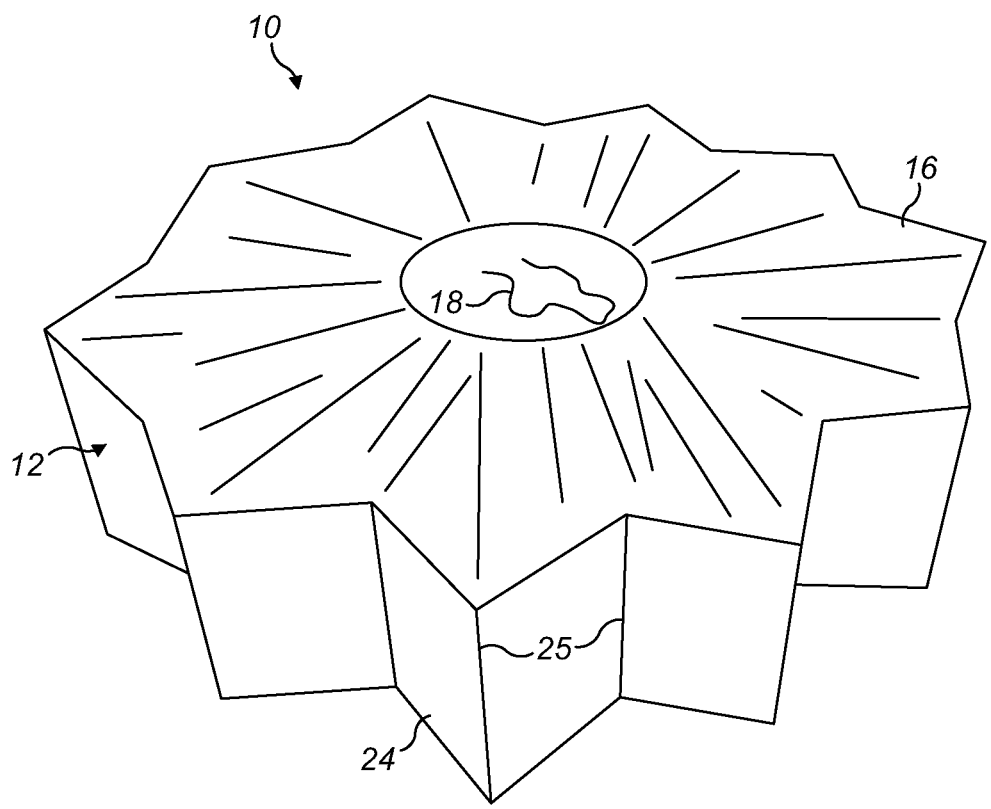
FIG. 1 is a schematic perspective view of a container in accordance with a first embodiment of the present invention.
Figure 2:
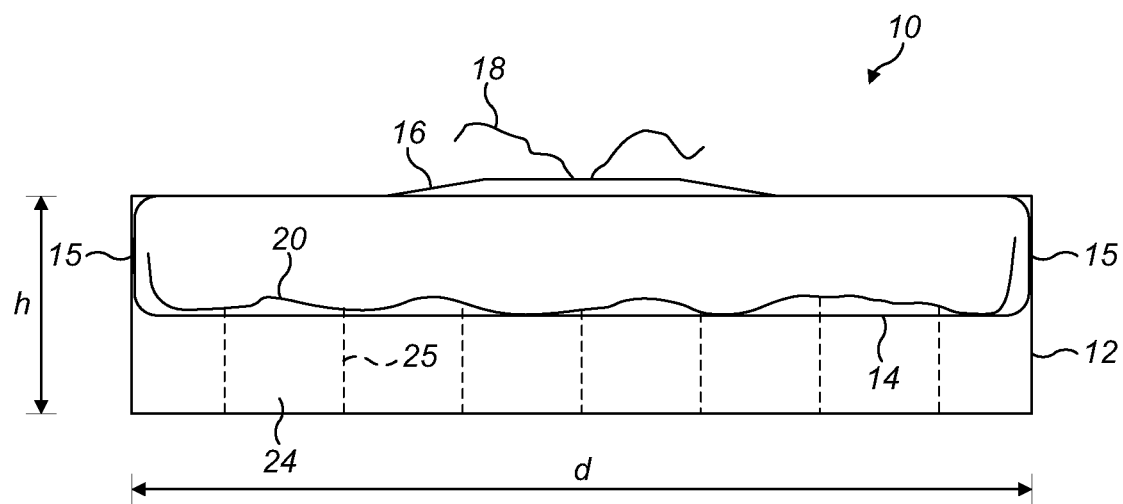
FIG. 2 is a cross-section of the device shown in FIG. 1.

With reference to FIGS. 1 and 2, a container 10 in accordance with the present invention comprises a continuous perimeter wall 12, a flexible base 14 and an openable and closeable flexible cover 16. Together these define an enclosure for receiving a medical device 22. The cover 16 may be closed by means of a drawstring 18. An absorbent cloth 20 may be placed within the container 10 on the flexible base 14 to absorb any fluids present on a medical device 22 placed in the container 10.

The perimeter wall 12 has a height h and defines the diameter d of the enclosure. The wall 12 is substantially rigid in the height dimension but can be contracted and expanded to provide an enclosure of different diameters. In the embodiment illustrated, the wall 12 is formed as a series of adjacent panels 24 with fold lines 25 between them. The panels 24 may be folded in a zig-zag or concertina-style manner. The wall 12 can be contracted when the panels 24 are folded so as to lie close to each other and expanded when the panels 24 are allowed to separate out.

Figure 3C:
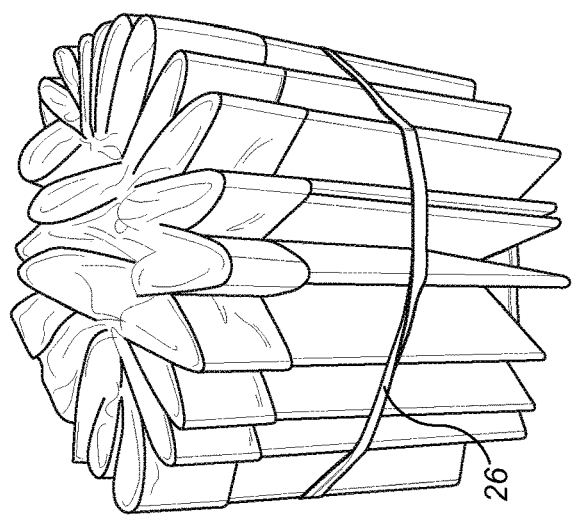
FIGS. 3a, 3b and 3c show the device in its compressed state, folded in alternative configurations.
Figure 3B:
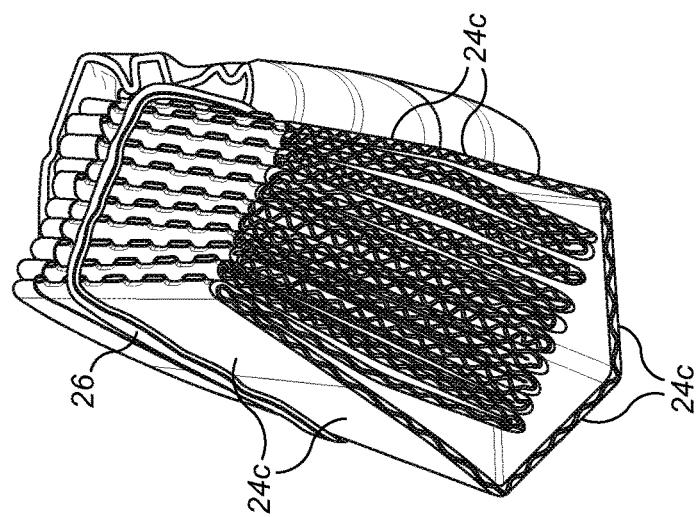
Figure 3A:
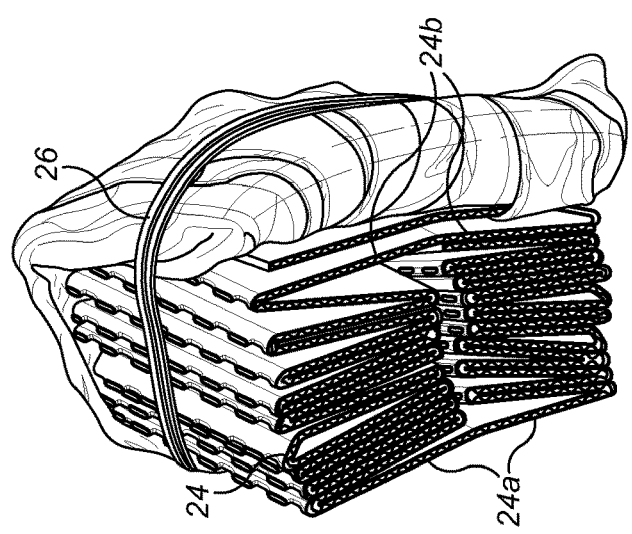
Figure 4:
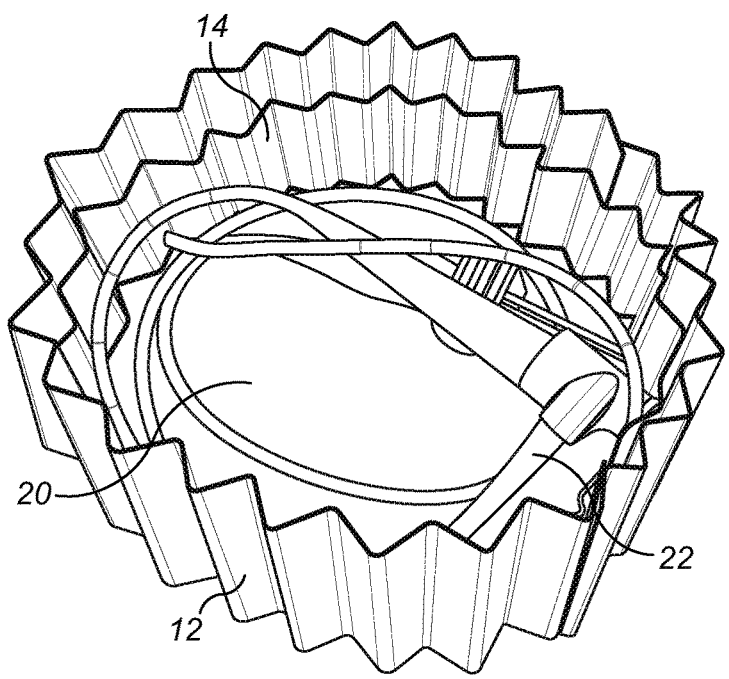
FIG. 4 shows the container expanded, with the cover removed for clarity, and a medical device placed within the container.

The wall 12 can be folded in different ways in order to contract it, as illustrated in FIGS. 3a-3c. In FIG. 3a, one pair of adjacent panels 24a is expanded out so that the pair is substantially flat. A corresponding pair of adjacent panels 24b on the opposite side is similarly expanded and lies flat. The remaining panels 24 are folded in two concertina rows between the flattened pairs 24a, 24b. In FIG. 3b, pairs of the panels 24 are folded flat and the flattened pairs concertinaed together, with six adjacent panels 24c folded out to join the two ends of the concertina row.

In FIG. 3c, all the panels 24 are contracted towards the centre.

In any of the contracted forms, the container 10 may be held by a fastener 26 such as an elastic band. The configurations shown in FIGS. 3a and 3b both produce a substantially rectangular package which is particularly space efficient. The configuration of FIG. 3c produces a substantially cylindrical package which is somewhat larger.

The wall 12 is dimensioned and sufficiently expandable that it can accommodate a desired medical instrument. In the case of an endoscope, it must provide an enclosure with a large enough diameter in which the endoscope can be placed without coiling it too tightly so that the internal channels and optical fibres within the endoscope are not subjected to unduly small bending radii. For example, the wall 12 can be dimensioned to produce an enclosure with an overall diameter in the order of 45 cm to 55 cm.

The wall 12 may be formed of any suitable material such as cardboard or plastic which provides a strong perimeter for the container 10, to protect a medical device 22 from side impact damage. In this example, it is formed of corrugated cardboard. The corrugations can be aligned vertically to provide the substantially rigid height dimension h and to allow formation of the fold lines 25 between corrugations. Corrugated cardboard is also a cheap, readily available and easily disposable material.

The base 14 of the container 10 is formed by a flexible sheet which is secured to the interior surface of the wall 12, for example by a line of adhesive 15 (shown schematically in FIG. 2). The flexible base 14 is thus suspended from the wall 12 in the form of a hammock. It is dimensioned such that it does not protrude below the bottom edge of the wall 12, even when a medical device 22 is placed upon it. This protects the medical device 22 from damage when the container 10 is placed on a surface. It is sufficiently strong to support the weight of a medical device 22 but is thin and flexible so that it can be folded up as the wall 12 is contracted. It is preferably formed of material such as plastic which is fluid impervious so that no leakage of fluid from the medical instrument 22 can occur.

In use, it may be desirable to place an absorbent cloth 20 within the container 10 on top of the base wall 14 for increased capacity to hold fluid.

Figure 5:
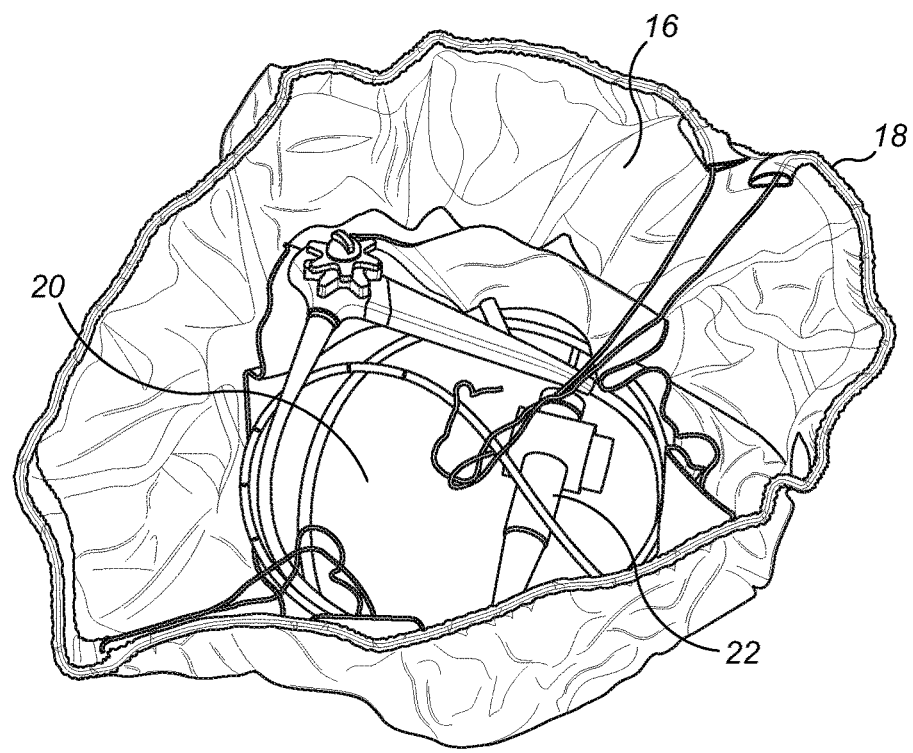
FIG. 5 shows the container in its expanded configuration, with the cover present and open and a medical device placed within the container.

The container 10 also includes a flexible cover 16 as shown in FIG. 5. This is of generally tubular form, with one circular edge secured to the wall 12, for example by the same line of adhesive 15 as the base 14, or a separate line. The other circular edge is free and provided with a drawstring 18. The cover 16 is dimensioned so that it can be opened out, with the free edge folded over to the exterior side of the perimeter wall 12, to allow easy access into the container 10. Once a medical instrument 22 is placed within the container 10, the drawstring 18 can be pulled to cause the cover 16 to close over the top of the container 10 as shown in FIG. 1. The drawstring 18 and flexible cover 16 may be configured to leave some central open area in the closed configuration, as illustrated in the schematic view of FIG. 1. Alternatively, it may be possible to pull in the drawstring 18 sufficiently tightly that there is no significant opening in the closed configuration.

The flexible cover 16 may be separate from the flexible base 14 or they may be integral with one another. In this case, they are effectively formed as a bag of thin flexible material which is joined to the wall 12, for example by the adhesive line 15. A lower part of the bag below the adhesive 15 then forms the flexible base 14 and an upper portion of the bag above the adhesive forms the flexible cover. The base 14 and cover 16 are formed of thin flexible material such as plastic. At least the cover 16 may be transparent so that the contents of the container 10 can be easily seen.

In use, the container 10 is initially held in its compressed state for storage. When required, any fastener 26 present is removed, the wall 12 is expanded and the cover 16 opened in order to expose the base wall 14. If desired, an absorbent cloth 20 can be laid inside the container 10 on the base 14. A medical instrument 22 can then be placed on top of the cloth 20. The cover 16 is then pulled in by the drawstring 18 in order to close it over the top of the medical device 22. In this state, the container 10 can be taken to a suitable location for cleaning and sterilisation. The cover 16 is opened by loosening the drawstring 18. The medical device 22 can be removed and the container 10 can then be disposed of.

Finger slots may be formed in the wall 12 to make it easier to carry the container 10 when a medical device is placed therein.

Figure 6A:
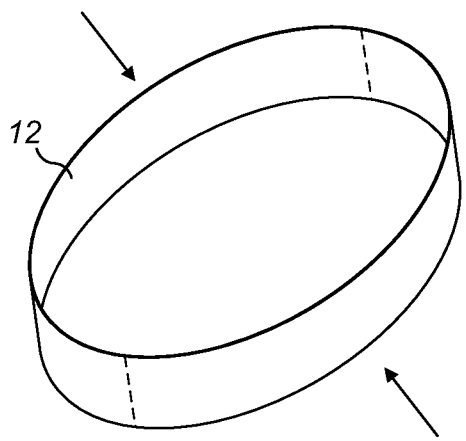
FIGS. 6a, 6b and 6c show an alternative embodiment of a compressible wall for the container of the present invention.
Figure 6B:
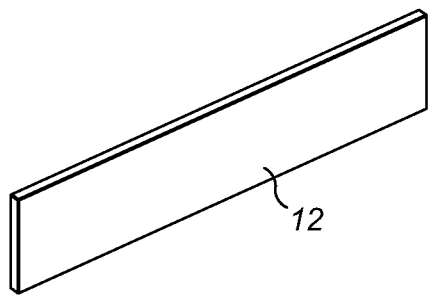
Figure 6C:
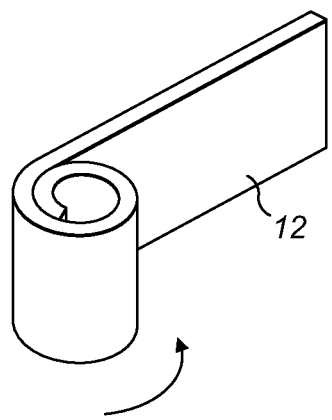

It will be appreciated that different forms of compressable and expandable container can be provided within the scope of the present invention. In particular, the perimeter wall 12 may have different configurations. One example is shown in FIGS. 6a, 6b and 6c. In this case, the wall 12 is formed of two panels 24 joined by fold lines 25. In the expanded configuration, each panel 24 thus forms a substantially semi-circular portion of the wall 12. These can be pressed together as shown in FIG. 6b to form a substantially flat item which can then be rolled up as shown in FIG. 6c, or folded, into a smaller package. In these diagrams, the flexible base wall and cover have been omitted for the sake of clarity.

The invention claimed is:

1. A container for carrying a medical instrument, comprising a perimeter wall having a height and defining an enclosure with a diameter, wherein the perimeter wall comprises a plurality of stiff panels adjacent to each other and with fold lines therebetween such that the perimeter wall is substantially rigid in its height dimension and protects a medical instrument when carried in the container from side impact damage, a flexible base formed by a thin flexible sheet which is secured to an interior surface of the perimeter wall for receiving a medical device, wherein the flexible base is suspended from the perimeter wall and hangs down in the form of a hammock and an openable and closable flexible cover attached to the perimeter wall, wherein the perimeter wall and the flexible base are compressible into a reduced diameter configuration for storage and expandable into an increased diameter configuration for receiving a medical device, and wherein in the expanded configuration a lowermost edge of the perimeter wall extends lower than the flexible base, even when the medical device is placed upon the base.

2. A container as claimed in claim 1, wherein the panels are folded concertina-style.

3. A container as claimed in claim 1, wherein the perimeter wall comprises two panels joined at their ends by fold lines.

4. A container as claimed in claim 1, wherein the cover comprises a thin flexible sheet.

5. A container as claimed in claim 4, wherein the cover comprises a substantially annular sheet with first and second circular edges, wherein the first circular edge is secured to the perimeter wall and the second circular edge is free and provided with closure means.

6. A container as claimed in claim 5, wherein the closure means comprises a drawstring arranged in the free edge of the cover.

7. A container as claimed in claim 1, wherein the perimeter wall defines two or more apertures for receiving a user's fingers to facilitate carrying the container.

8. A container as claimed in claim 1, wherein the perimeter wall is formed of corrugated cardboard.

9. A container as claimed in claim 1, further comprising a fluid absorbent sheet located within the container.

10. A container as claimed in claim 4, wherein the flexible base and the flexible cover are integral with one another.

* * * * *